United States Patent [19]
Gegg et al.

[11] Patent Number: 5,900,404
[45] Date of Patent: May 4, 1999

[54] CHEMICAL MODIFICATION OF PROTEINS TO IMPROVE BIOCOMPATIBILITY AND BIOACTIVITY

[75] Inventors: Colin Gegg; Olaf Kinstler, both of Newbury Park, Calif.

[73] Assignee: Amgen Inc., Thousand Oaks, Calif.

[21] Appl. No.: 08/911,224

[22] Filed: Aug. 15, 1997

[51] Int. Cl.⁶ .................................................. A61K 38/00
[52] U.S. Cl. ............................... 514/12; 514/2; 530/324; 530/412; 530/402
[58] Field of Search ..................................... 530/324, 412, 530/402; 514/12, 21

[56] References Cited

U.S. PATENT DOCUMENTS 4,955,857  9/1990  Sheltigar ........................................ 604/5

OTHER PUBLICATIONS

Holcenberg et al., The Journal of Biological Chemistry, vol. 250, No. 11, 4165–4170 (1975).

*Primary Examiner*—F. T. Moezie
*Attorney, Agent, or Firm*—Craig A. Crandall; Ron L. Levy; Steven M. Odre

[57] ABSTRACT

The present invention broadly relates to chemical modification of biologically active proteins or analogs thereof. More specifically, the present invention describes novel methods for site-specific chemical modification of various proteins, and resultant compositions having improved biocompatibility and bioactivity.

3 Claims, 12 Drawing Sheets

CHEMICAL MODIFICATION OF PROTEINS TO IMPROVE BIOCOMPATIBILITY AND BIOACTIVITY

FIELD OF THE INVENTION

The present invention broadly relates to chemical modification of biologically active proteins or analogs thereof (the term "protein" as used herein is synonymous with "polypeptide" or "peptide" unless otherwise indicated). More specifically, the present invention describes novel methods for site-specific chemical modifications of various proteins, and resultant compositions.

BACKGROUND OF THE INVENTION

Due to recent advances in genetic and cell engineering technologies, proteins known to exhibit various pharmacological actions in vivo are capable of production in large amounts for pharmaceutical applications. Such proteins include erythropoietin (EPO), granulocyte colony-stimulating factor (G-CSF), interferons (alpha, beta, gamma, consensus), tumor necrosis factor binding protein (TNFbp), interleukin-1 receptor antagonist (IL-1ra), brain-derived neurotrophic factor (BDNF), kerantinocyte growth factor (KGF), stem cell factor (SCF), megakaryocyte growth differentiation factor (MGDF), osteoprotegerin (OPG), glial cell line derived neurotrophic factor (GDNF) and obesity protein (OB protein). OB protein may also be referred to herein as leptin.

Leptin is active in vivo in both ob/ob mutant mice (mice obese due to a defect in the production of the OB gene product) as well as in normal, wild type mice. The biological activity manifests itself in, among other things, weight loss. See generally, Baringa, "Obese" Protein Slims Mice, *Science* 269: 475–476 (1995) and Friedman, "The Alphabet of Weight Control," *Nature* 385: 119–120 (1997). It is known, for instance, that in ob/ob mutant mice, administration of leptin results in a decrease in serum insulin levels, and serum glucose levels. It is also known that administration of leptin results in a decrease in body fat. This was observed in both ob/ob mutant mice, as well as non-obese normal mice. Pelleymounter et al., *Science* 269: 540–543 (1995); Halaas et al., *Science* 269: 543–546 (1995). See also, Campfield et al., *Science* 269: 546–549 (1995) (Peripheral and central administration of microgram doses of leptin reduced food intake and body weight of ob/ob and diet-induced obese mice but not in db/db obese mice.) In none of these reports have toxicities been observed, even at the highest doses.

Preliminary leptin induced weight loss experiments in animal models predict the need for a high concentration leptin formulation with chronic administration to effectively treat human obesity. Dosages in the milligram protein per kilogram body weight range, such as 0.5 or 1.0 mg/kg/day or below, are desirable for injection of therapeutically effective amounts into larger mammals, such as humans. An increase in protein concentration is thus necessary to avoid injection of large volumes, which can be uncomfortable or possibly painful to the patient.

Unfortunately, for preparation of a pharmaceutical composition for injection in humans, it has been observed that the leptin amino acid sequence is insoluble at physiologic pH at relatively high concentrations, such as above about 2 mg active protein/milliliter of liquid. The poor solubility of leptin under physiological conditions appears to contribute to the formation of leptin precipitates at the injection site in a concentration dependent manner when high dosages are administered in a low pH formulation. Associated with the observed leptin precipitates is an inflammatory response at the injection site which includes a mixed cell infiltrate characterized by the presence of eosinophils, macrophages and giant cells.

To date, there have been no reports of stable preparations of human OB protein at concentrations of at least about 2 mg/ml at physiologic pH, and further, no reports of stable concentrations of active human OB protein at least about 50 mg/ml or above. The development of leptin forms which would allow for high dosage without the aforementioned problems would be of great benefit. It is therefore one object of the present invention to provide improved forms of leptin by way of site-specific chemical modification of the protein.

There are several methods of chemical modification of useful therapeutic proteins which have been reported. One such method, succinylation, involves the conjugation of one or more succinyl moieties to a biologically active protein. Classic approaches to succinylation traditionally employ alkaline reaction conditions with very large excesses of succinic anhydride. The resultant succinyl-protein conjugates are typically modified at multiple sites, often show altered tertiary and quaternary structures, and occasionally are inactivated. The properties of various succinylated proteins are described in Holcenberg et al., *J. Biol. Chem,* 250:4165–4170 (1975), and WO 88/01511 (and references cited therein), published Mar. 10, 1988. Importantly, none of the cited references describe methods wherein the biologically active protein is monosuccinylated exclusively at the N-terminus of the protein, and wherein the resultant composition exhibits improved solubility and improved injection site toxicity's.

Diethylenetriaminepentaacetic acid anhydride (DTPA) and ethylenediaminetetraacetic acid dianhydride (hereinafter referred to as $EDTA^2$) have classically been used to introduce metal chelation sites into proteins for the purpose of radiolabeling. Similar to succinylation, modification with DTPA and/or $EDTA^2$ typically occurs at multiple sites throughout the molecule and changes the charge and isoelectric point of the modified protein. To date, there have been no reports of DTPA- and/or $EDTA^2$-protein monomers and dimers which exhibit improved solubility and improved injection site toxicity's.

SUMMARY OF THE INVENTION

The present invention relates to substantially homogenous preparations of chemically modified proteins, e.g. leptin, and methods therefor. Unexpectedly, site-specific chemical modification of leptin demonstrated advantages in bioavailibility and biocompatibility which are not seen in other leptin species. Importantly, the methods described herein are broadly applicable to other proteins (or analogs thereof), as well as leptin. Thus, as described below in more detail, the present invention has a number of aspects relating to chemically modifying proteins (or analogs thereof) as well as specific modifications of specific proteins.

In one aspect, the present invention relates to a substantially homogenous preparation of mono-succinylated leptin (or analog thereof) and related methods. Importantly, the method described results in a high yield of monosuccinylated protein which is modified exclusively at the N-terminus, thereby providing processing advantages as compared to other species. And, despite the modest N-terminal modification, the monosubstituted succinyl-leptin unexpectedly demonstrated: 1) a substantial improvement in solubility; 2) preservation of secondary structure, in vitro receptor binding activity and in vivo bioefficacy; and 3)

amelioration of the severe injection site reactions observed with administration of high concentrations of unmodified leptin.

In another aspect, the present invention relates to substantially homogenous preparations of DTPA-leptin monomers and dimers and related methods. When reacted with leptin at neutral pH and a low stoichiometric excess of DTPA:protein, this reagent unexpectedly forms a single crosslink between the N-termini of two leptin molecules in high yield. When the monosubstituted DTPA-leptin monomer and dimer are isolated, both show substantially increased solubility's relative to the unmodified protein. Both forms also demonstrate preservation of in vitro receptor binding activity and in vivo bioefficacy. Significantly, the dimeric form of monosubstituted DTPA-leptin did not precipitate when injected at high concentration in PBS and demonstrated strong improvement in the injection site reactions over those observed with the unmodified leptin.

In yet another aspect, the present invention relates to substantially homogenous preparations of EDTA dianhydride ($EDTA^2$)-leptin monomers and dimers and related methods. Similar to DTPA in structure, $EDTA^2$ crosslinks leptin efficiently through the N-terminus when allowed to react at neutral pH in a substoichiometric excess. The isolated $EDTA^2$-leptin dimer demonstrates dramatically enhanced solubility relative to unmodified leptin and maintains full in vitro receptor binding activity and in vivo bioactivity. Furthermore, the $EDTA^2$-leptin conjugate did not precipitate at the injection site when dosed at high concentration in PBS and demonstrated substantial improvement in the adverse injection site reactions observed with the unmodified leptin.

DETAILED DESCRIPTION

Figure 1:
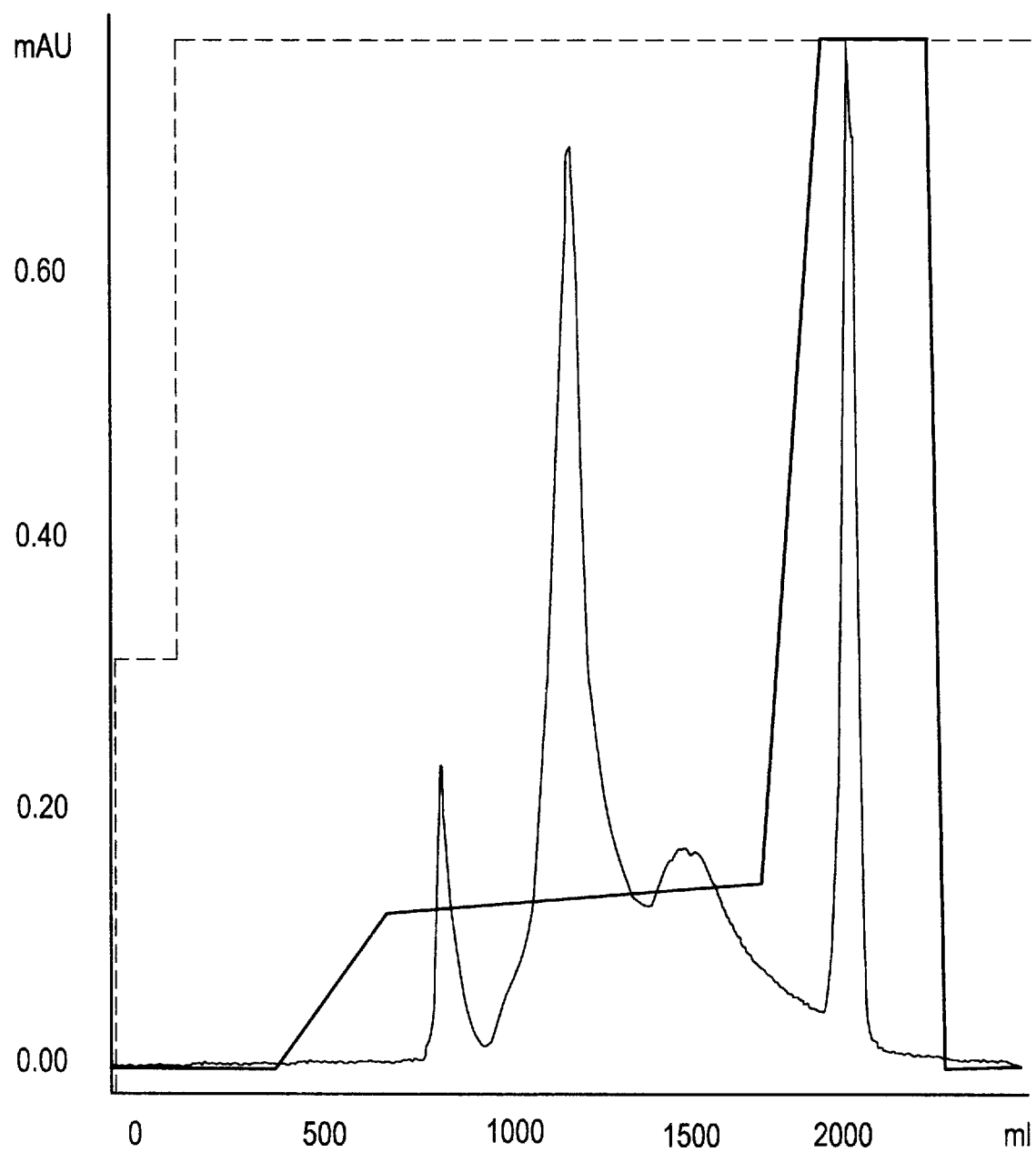
FIG. 1 is a chromatogram of a anion exchange chromatography separation of succinylated leptin. Absorbance at 280 nm is plotted vs. elution volume in mL. The monosuccinylated leptin peak is marked by (*).

The present invention relates to substantially homogenous preparations of chemically modified proteins, and methods therefor. "Substantially homogenous" as used herein means that the only chemically modified proteins observed are those having one "modifier" (e.g., DTPA, $EDTA^2$, succinyl) moiety. The preparation may contain unreacted (i.e., lacking modifier moiety) protein. As ascertained by peptide mapping and N-terminal sequencing, one example below provides for a preparation which is at least 90% modified protein, and at most 10% unmodified protein. Preferably, the chemically modified material is at least 95% of the preparation (as in the working example below) and most preferably, the chemically modified material is 99% of the preparation or more. The chemically modified material has biological activity. The present "substantially homogenous" monosuccinylated leptin, DTPA-leptin, and $EDTA^2$-leptin preparations provided herein are those which are homogenous enough to display the advantages of a homogenous preparation, e.g., ease in clinical application in predictability of lot to lot pharmacokinetics.

As used herein, biologically active agents refers to recombinant or naturally occurring proteins, whether human or animal, useful for prophylactic, therapeutic or diagnostic application. The biologically active agent can be natural, synthetic, semi-synthetic or derivatives thereof. In addition, biologically active agents of the present invention can be perceptible. A wide range of biologically active agents are contemplated. These include but are not limited to hormones, cytokines, hematopoietic factors, growth factors, antiobesity factors, trophic factors, anti-inflammatory factors, and enzymes (see also U.S. Pat. No. 4,695,463 for additional examples of useful biologically active agents). One skilled in the art will readily be able to adapt a desired biologically active agent to the compositions of present invention.

Such proteins would include but are not limited to interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582, 823, and PCT Publication No. 94/17185, hereby incorporated by reference including drawings), stem cell factor (PCT Publication Nos. 91/05795, 92/17505 and 95/17206, hereby incorporated by reference including drawings), and leptin (OB protein) (see PCT publication Nos. 96/40912, 96/05309, 97/00128, 97/01010 and 97/06816 hereby incorporated by reference including figures). PCT publication No. WO 96/05309, published Feb. 22, 1996, entitled, "Modulators of Body Weight, Corresponding Nucleic Acids and Proteins, and Diagnostic and Therapeutic Uses Thereof" fully sets forth OB protein and related compositions and methods, and is herein incorporated by reference. An amino acid sequence for human OB protein is set forth at WO 96/05309 Seq. ID Nos. 4 and 6 (at pages 172 and 174 of that publication), and the first amino acid residue of the mature protein is at position 22 and is a valine residue. The mature protein is 146 residues (or 145 if the glutamine at position 49 is absent, Seq. ID No. 4).

In addition, biologically active agents can also include but are not limited to insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein. The term proteins, as used herein, includes peptides, polypeptides, consensus molecules, analogs, derivatives or combinations thereof.

In general, comprehended by the invention are pharmaceutical compositions comprising effective amounts of chemically modified protein, or derivative products, together with pharmaceutically acceptable diluents, preservatives, solubilizers, emulsifiers, adjuvants and/or carriers needed for administration. (See PCT 97/01331 hereby incorporated by reference.) The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, PA., pgs. 1435–1712 (1990)). The pharmaceutical compositions of the present invention may be administered by oral and non-oral preparations (e.g., intramuscular, subcutaneous, transdermal, visceral, IV (intravenous), IP (intraperitoneal), intraarticular, placement in the ear, ICV (intracerebralventricular), IP (intraperitoneal), intraarterial, intrathecal, intracapsular, intraorbital, injectable, pulmonary, nasal, rectal, and uterine-transmucosal preparations).

Therapeutic uses of the compositions of the present invention depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like interferons (see, U.S. Pat. Nos. 5,372,808, 5,541,293, hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,999,291, 5,581,476, 5,582,823, 4,810, 643 and PCT Publication No. 94/17185, hereby incorporated by reference including drawings), stem cell factor (PCT Publication Nos. 91/05795, 92/17505 and 95/17206, hereby incorporated by reference including drawings), and the OB protein (see PCT publication Nos. 96/40912, 96/05309, 97/00128, 97/01010 and 97/06816 hereby incorporated by reference including figures). In addition, the present compositions may also be used for manufacture of one or more medicaments for treatment or amelioration of the conditions the biologically active agent is intended to treat.

The principal embodiment of the method for making the substantially homogenous preparation of monosuccinylated protein comprises: (a) reacting a protein with 3–7 fold molar excess of succinic anhydride; (b) stirring the reaction mixture 2–16 hours at 4° C.; (c) dialyzing said mixture against 20 mM Tris-HCl, pH 7.2; and (d) isolating said monosuccinylated protein. Optionally, the method can comprise, just after step (b), the steps of: adding solid hydroxylamine to said mixture while maintaining the pH above 6.5 until said hydroxylamine is completely dissolved, followed by elevating the pH to 8.5 using 5N NaOH, followed by stirring said mixture another 1–2 hours at 4° C. The general process is shown schematically in Example 1.

The principal embodiment of the method for making the substantially homogenous preparation of DTPA-protein comprises: (a) reacting a protein with 1–5 fold molar excess of DTPA; (b) stirring the reaction mixture 2–16 hours at 4° C.; (c) dialyzing said mixture against 20 mM Tris-HCl, pH 7.2; and (d) isolating said DTPA-protein. The general process is shown schematically in Example 1.

The principal embodiment of the method for making the substantially homogenous preparation of $EDTA^2$-protein comprises: (a) reacting a protein with 0.5–5 fold molar excess of $EDTA^2$; (b) stirring the reaction mixture 2–16 hours at 4° C.; (c) filtering said reaction mixture; (d) concentrating said reaction mixture; and (e) isolating said $EDTA^2$-protein. The general process is shown schematically in Example 1.

The following examples are offered to more fully illustrate the invention, but are not to be construed as limiting the scope thereof. Example 1 describes the preparation of monosuccinylated leptin, monosubstituted DTPA-leptin monomers and dimers, and $EDTA^2$-leptin monomers and dimers. Example 2 describes the physiochemical characterization of the modified leptin species prepared in Example 1. Example 3 describes the receptor binding studies performed on the modified leptin species prepared in Example 1. Example 4 describes the solubility testing performed on the modified leptin species prepared in Example 1. Example 5 describes the in vivo bioactivity studies performed on the modified leptin species prepared in Example 1. Example 6 describes the injection site evaluation performed on the modified leptin species prepared in Example 1.

EXAMPLE 1

This example describes the preparation of monosuccinylated leptin, monosubstituted DTPA-leptin monomers and dimers, and EDTA$^2$-leptin monomers and dimers.

1. Monosuccinylated leptin

The protein succinylation method of the present invention can be generally depicted as follows:

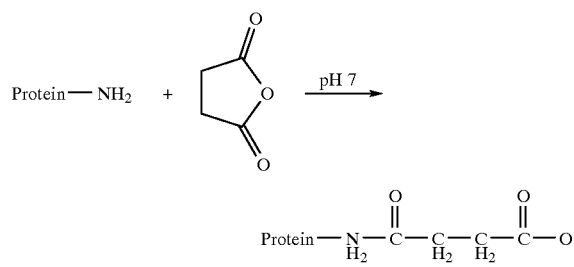

Recombinant human-methionyl-leptin (rhu-met-leptin) protein (prepared as described in Materials and Methods, infra) at 2–3 mg/mL in 20 mM NaHPO$_4$, pH 7.0, was reacted with 3–7 fold molar excess of solid succinic anhydride (Sigma Chemical, St. Louis, Mo.), with a 5 fold molar excess preferred, and the reaction stirred 2–16 hours at 4° C. Solid hydroxylamine (Sigma Chemical, St. Louis, Mo.) is then added to the reaction while maintaining the pH above 6.5. After the hydroxylamine has dissolved completely the pH is elevated to 8.5 using 5N NaOH and the reaction allowed to stir another 1–2 hours at 4° C. (the hydroxylamine step may be omitted with a small decrease in yield). Finally, the reaction is dialyzed against 20 mM Tris-HCl, pH 7.2.

Figure 2:
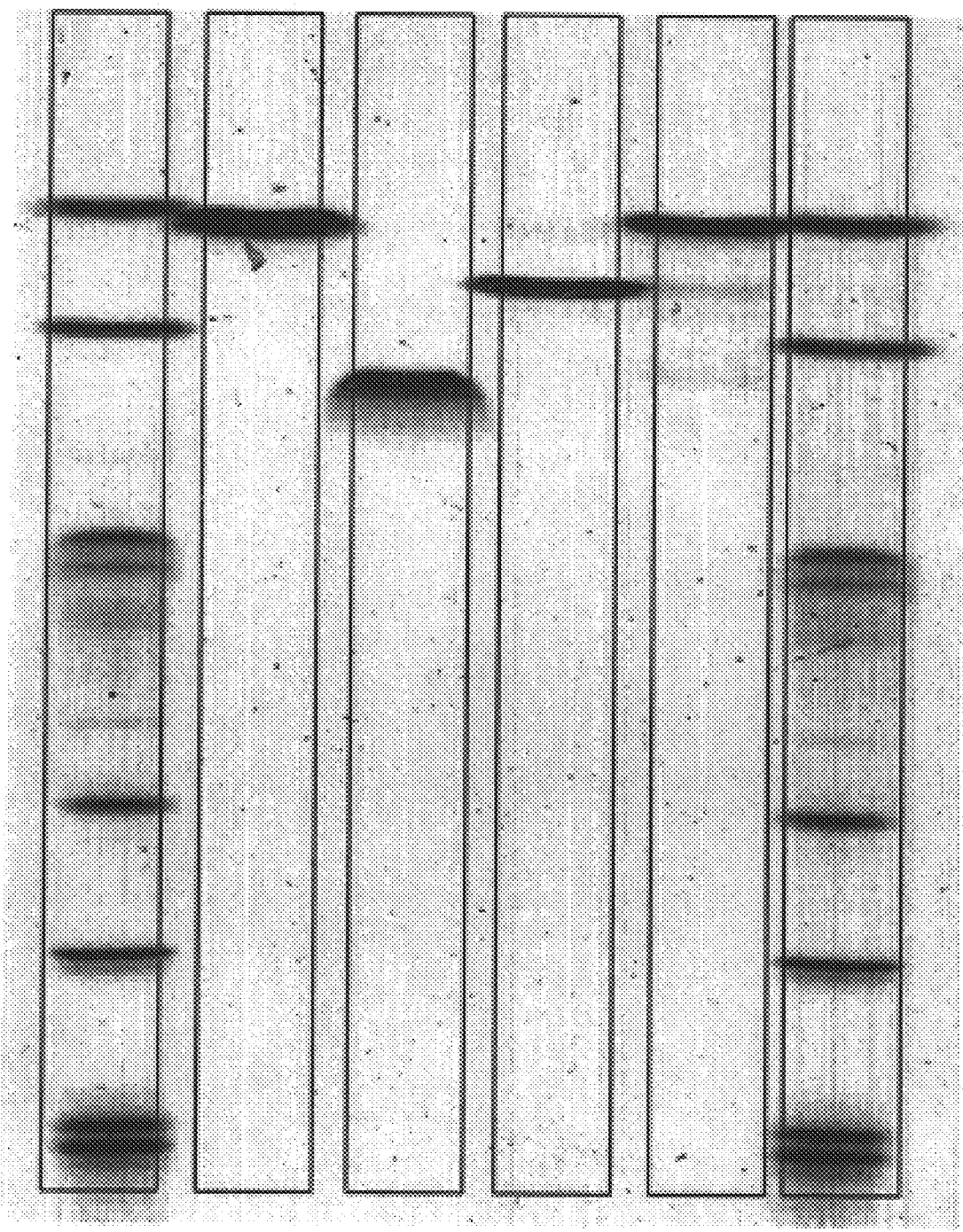
FIG. 2 is a pH 3–7 IEF-PAGE gel depicting unmodified leptin (lane 2), succinylated leptin (lane 3), DTPA modified leptin dimer (lane 4) and $EDTA^2$ modified leptin dimer (lane 5). Lanes 1 and 6 are isoelectric point markers.

The monosuccinylated rhu-met-leptin is isolated by anion exchange chromatography with a High Performance Sepharose Q column (Pharmacia, Piscataway, N.J.) in 20 mM Tris, pH 7.2, with a 0–0.5M NaCl gradient (see FIG. 1). The product is recognized in the eluant by an isoelectric shift of −0.7 pI units observed with isoelectric focusing (IEF) PAGE using a 5% polyacrylamide, pH 3–7 gel (Novex, Inc., San Diego, Calif.) (FIG. 2). Final recovery of monosuccinylated rhu-met-leptin is typically 45–47%.

2. Monosubstituted DTPA-leptin monomers and dimers

The DTPA modification method of the present invention can be generally depicted as follows:

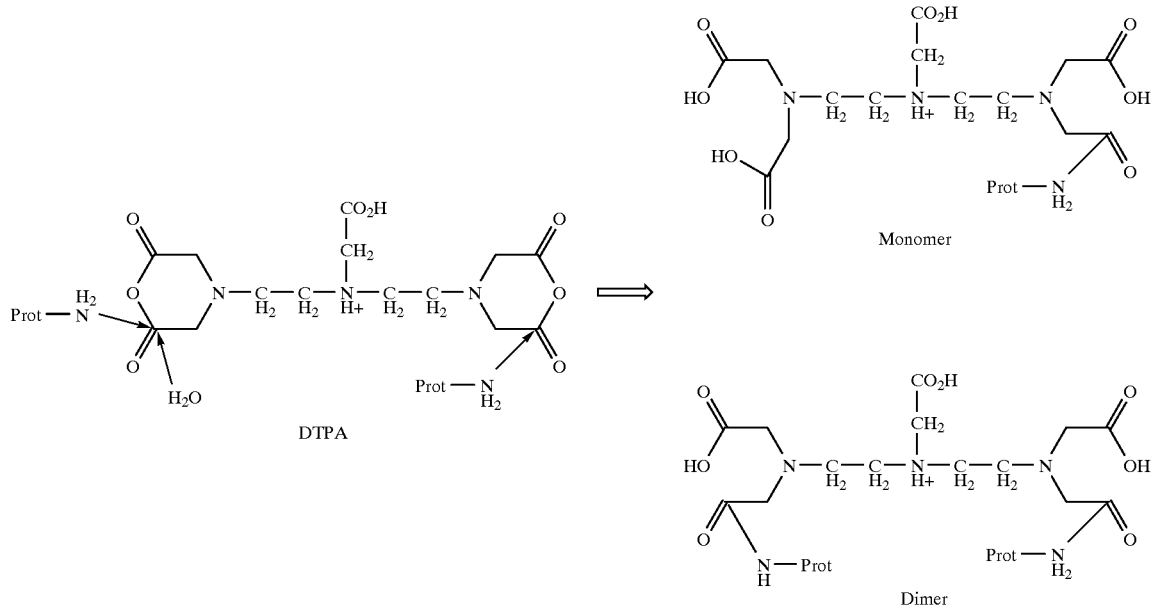
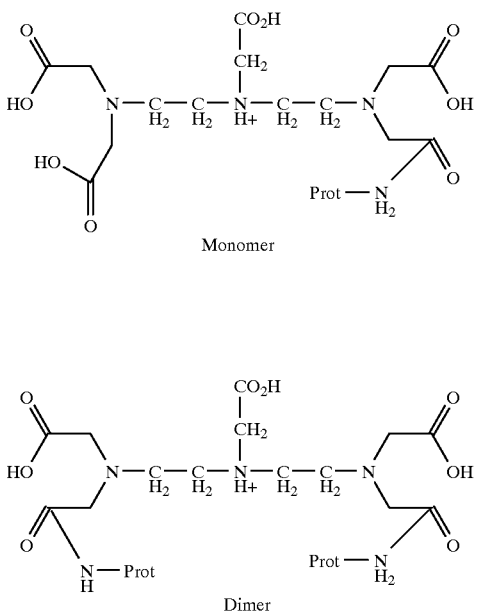

Figure 3:
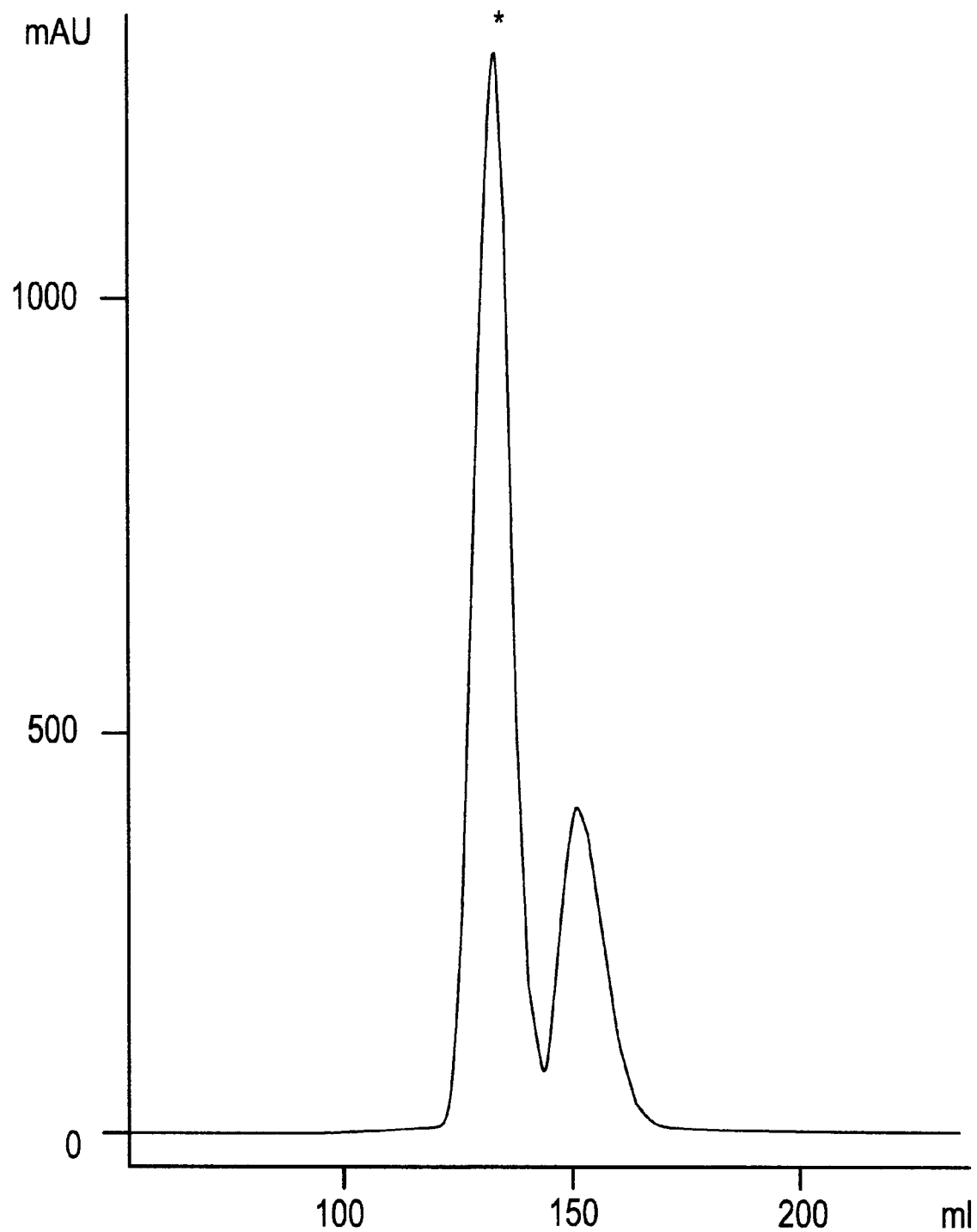
FIG. 3 is a chromatogram of a size exclusion chromatography separation of DTPA crosslinked leptin monomer and dimer. Absorbance at 280 nm is plotted vs. elution volume in mL. The dimeric form of monosubstituted DTPA-leptin is marked by (*)

Recombinant human-methionyl-leptin (rhu-met-leptin) protein (prepared as described in Materials and Methods, infra) at 2–3 mg/mL in 20 mM NaHPO$_4$, pH 7.0, was reacted with a 1–5 fold molar excess of solid DTPA (Sigma Chemical, St. Louis, Mo.), with 2–3 fold molar excess preferred, and the reaction stirred 2–16 hours at 4° C. Finally, the reaction is dialyzed against 20 mM Tris-HCl, pH 7.2. The DTPA modified rhu-met-leptin is isolated by anion exchange chromatography with a High Performance Sepharose Q column (Pharmacia, Piscataway, N.J.) in 20 mM Tris, pH 7.2, with a 0–0.5M NaCl gradient. Alternatively, monomeric and dimeric forms of monosubstituted DTPA-rhu-met-leptin or rhu-met-leptin are separated by size exclusion chromatography on a Sephacryl 100 column (Pharmacia, Piscataway, N.J.) in PBS (Life Technologies, Grand Island, N.Y.) (see FIG. 3). The products are recognized in the eluant by an isoelectric shift observed with the monomeric DTPA-leptin by isoelectric focusing (IEF) PACE using a 5% polyacrylamide, pH 3–7 gel (Novex, Inc., San Diego, Calif.) (FIG. 2) or the mass increase of a crosslinked dimer observed with SDS-PAGE using a 4–20% polyacrylamide gel (Novex, Inc., San Diego, Calif.) (see FIG. 4). Final recovery of DTPA-rhu-met-leptin dimer is approximately 30%.

3. Monosubstituted EDTA$^2$leptin monomers and dimers

The EDTA$^2$ modification method of the present invention can be generally depicted as follows:

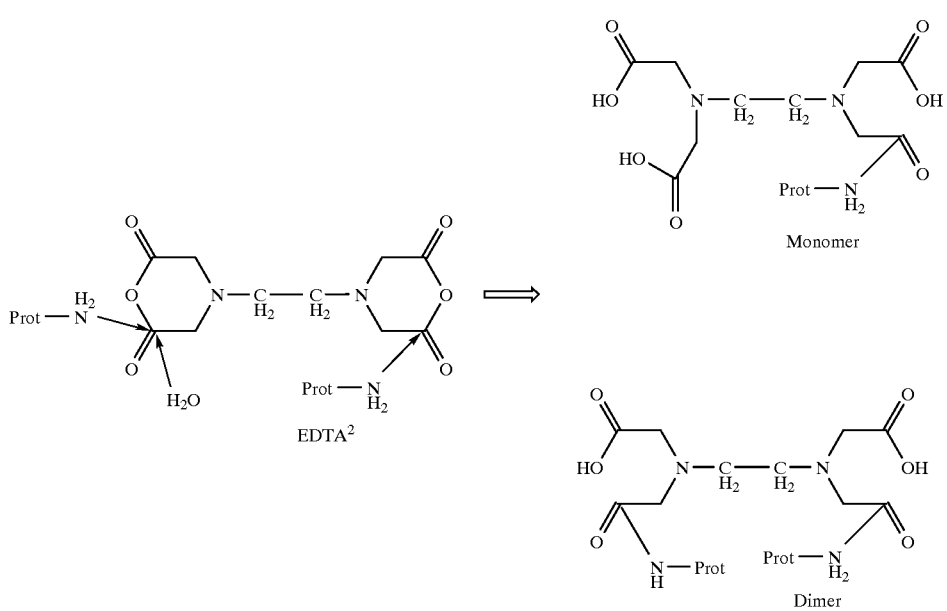

Recombinant human-methionyl-leptin (rhu-met-leptin) protein (prepared as described in Materials and Methods, infra) at 2–3 mg/mL in 20 mM NaHPO$_4$, pH 7.0, was reacted with a 0.5–5 fold molar excess of EDTA$^2$ (Aldrich Chemical Co., Milwaukee, Wis.) either as a solid or dissolved in DMSO, with 0.75 fold molar excess EDTA$^2$ in DMSO preferred, and the reaction stirred 2–16 hours at 4° C.

Figure 4:
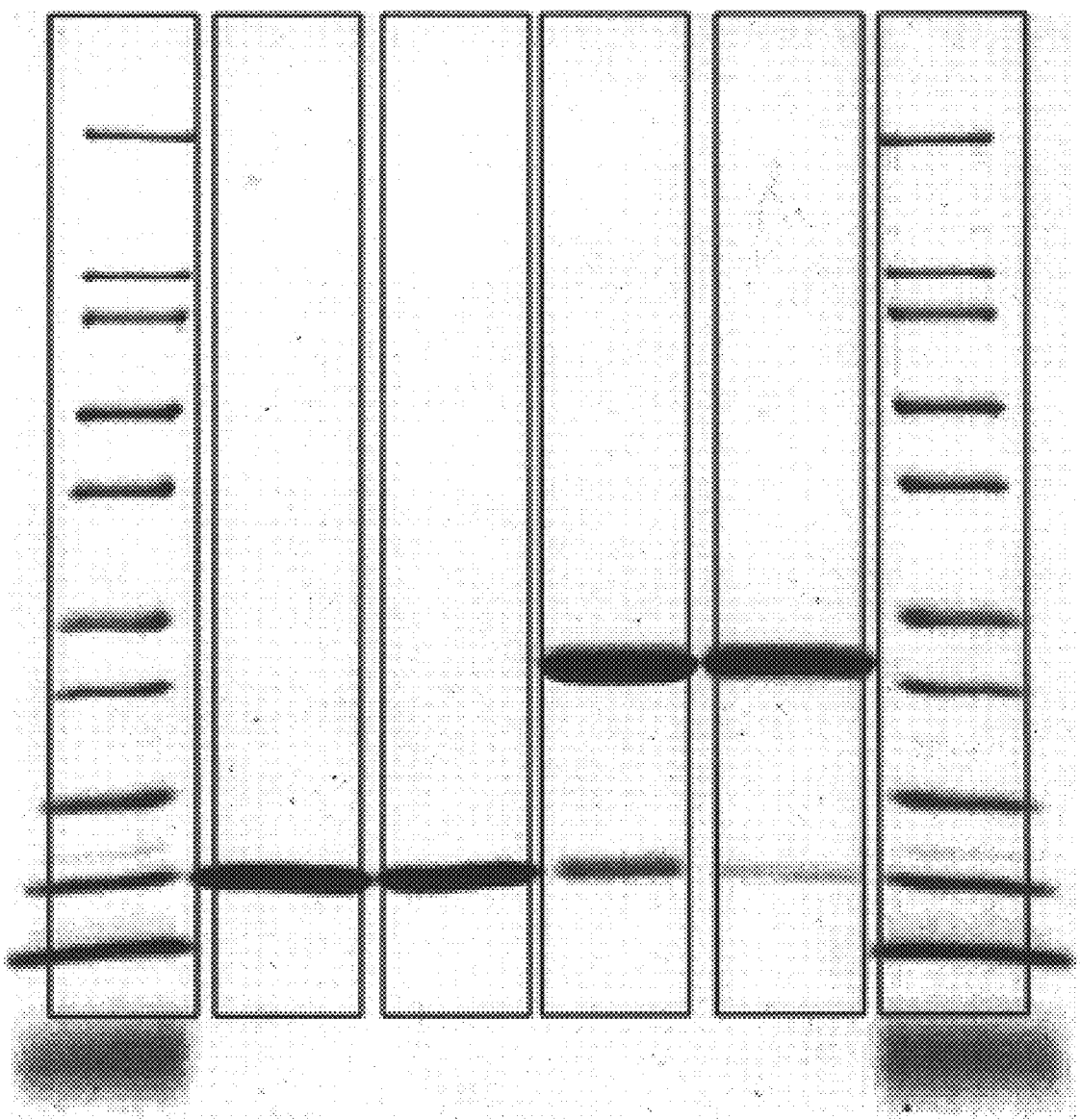
FIG. 4 is a 4–20% SDS-PAGE gel depicting unmodified leptin (lane 2), succinylated leptin (lane 3), DTPA modified leptin dimer (lane 4) and $EDTA^2$ modified leptin dimer (lane 5). Lanes 1 and 6 are molecular weight markers.
Figure 5:
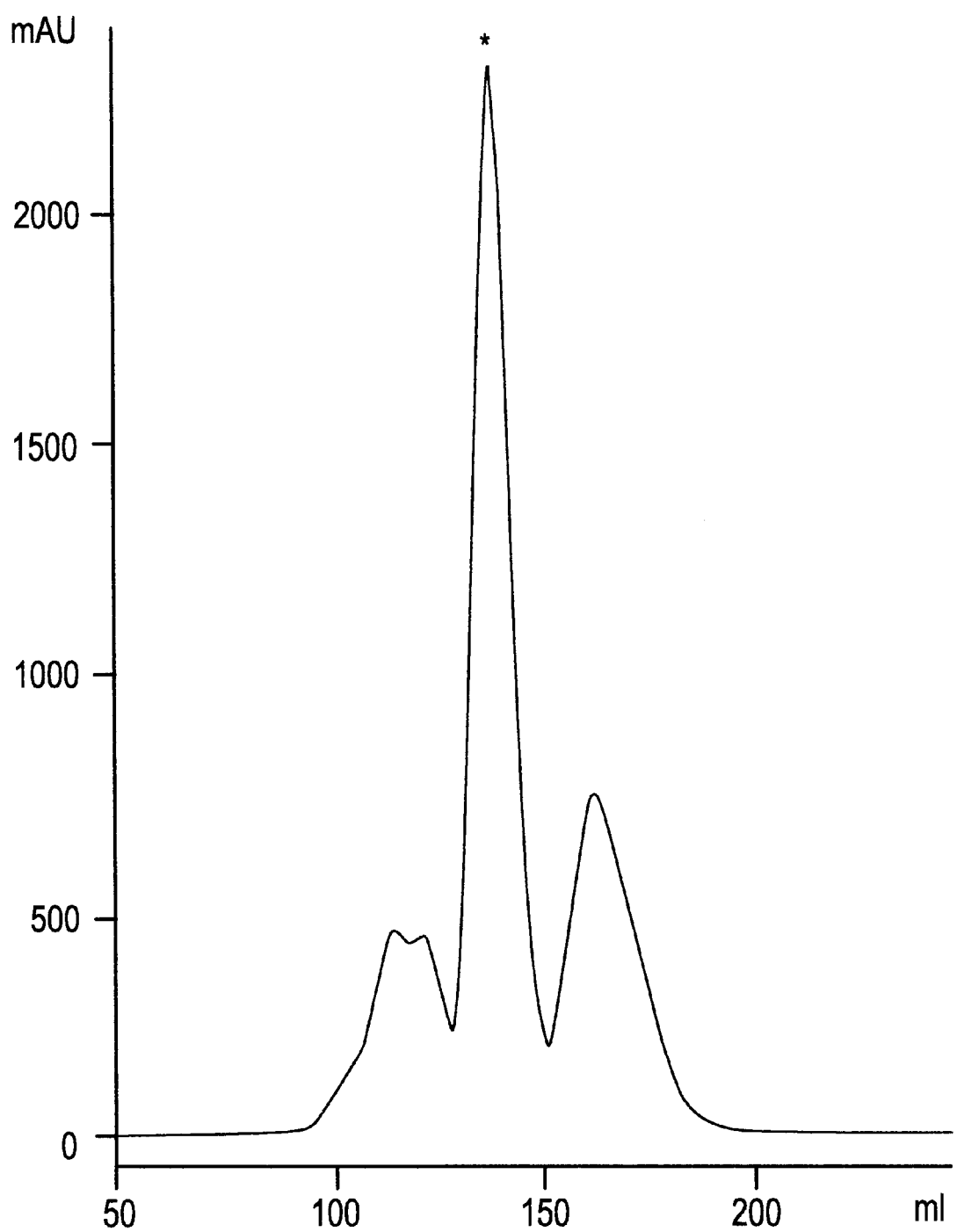
FIG. 5 is a chromatogram of a size exclusion chromatography separation of $EDTA^2$ crosslinked leptin monomer and dimer. Absorbance at 280 nm is plotted vs. elution volume in mL. The dimeric form of monosubstituted $EDTA^2$-leptin is marked by (*).

The reaction is then filtered through a 0.45 micron filter (Nalgene), concentrated by stirred cell over 10 kDa molecular weight cutoff membrane to ~20 mg/mL and the monomeric and dimeric forms of monosubstituted EDTA$^2$-rhu-met-leptin then separated by size exclusion chromatography on a Sephacryl 100 column (Pharmacia, Piscataway, N.J.) equilibrated in PBS (see FIG. 5). Alternatively, the reaction may be purified by hydrophobic interaction chromatography using a High Performance Phenyl-Sepharose column (Pharmacia, Piscataway, N.J.) eluted with a 0.8–0M ammonium sulfate gradient in 20 mM NaHPO$_4$, pH 7.0. The products are recognized in the eluant by an isoelectric shift observed with the monomeric EDTA$^2$-rhu-met-leptin by isoelectric focusing (IEF) PAGE using a 5% polyacrylamide, pH 3–7 gel (Novex, Inc., San Diego, Calif.) (FIG. 2) or the mass increase of a crosslinked dimer observed with SDS-PAGE using a 4–20% polyacrylamide gel (Novex, Inc., San Diego, Calif.) (FIG. 4). Final recovery of EDTA$^2$-rhu-met-leptin dimer exceeds 50%.

EXAMPLE 2

This example describes the physiochemical characterization of the leptin conjugates prepared in Example 1. Modification of succinyl-leptin, DTPA-leptin monomers and dimers, and EDTA$^2$-leptin monomers and dimers was evaluated by a combination of peptide mapping of Lys-C digests on reverse phase HPLC, MALDI-TOF mass spectrometry and peptide sequencing.

Figure 6:
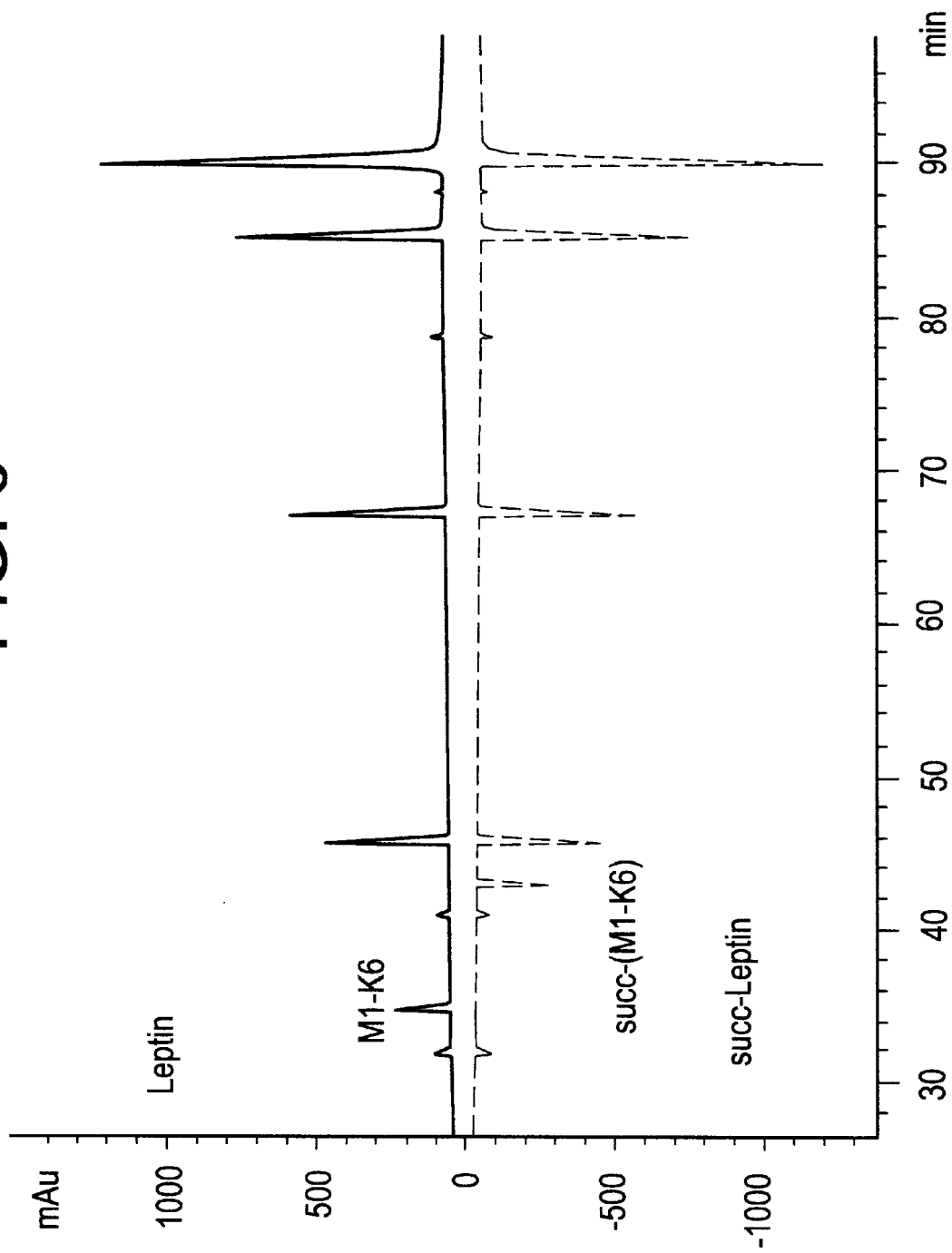
FIG. 6 is a reverse phase HPLC chromatogram of Lys-C digests showing retention time shifts resulting from chemical modifications of the N-terminal peptide (M1–K6) by succinic anhydride.
Figure 7:
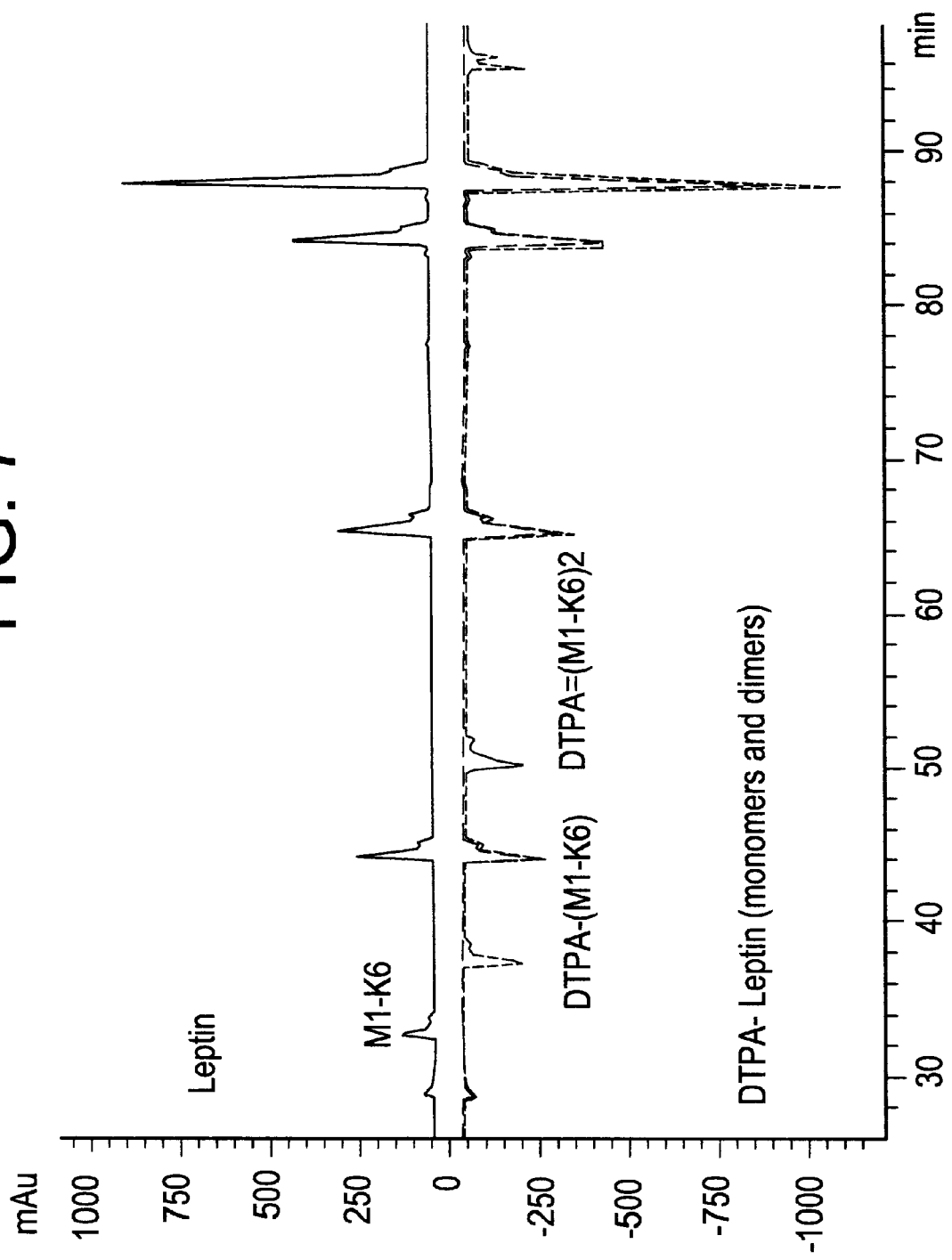
FIG. 7 is a reverse phase HPLC chromatogram of Lys-C digests showing retention time shifts resulting from chemical modifications of the N-terminal peptide (M1–K6) by DTPA.
Figure 8:
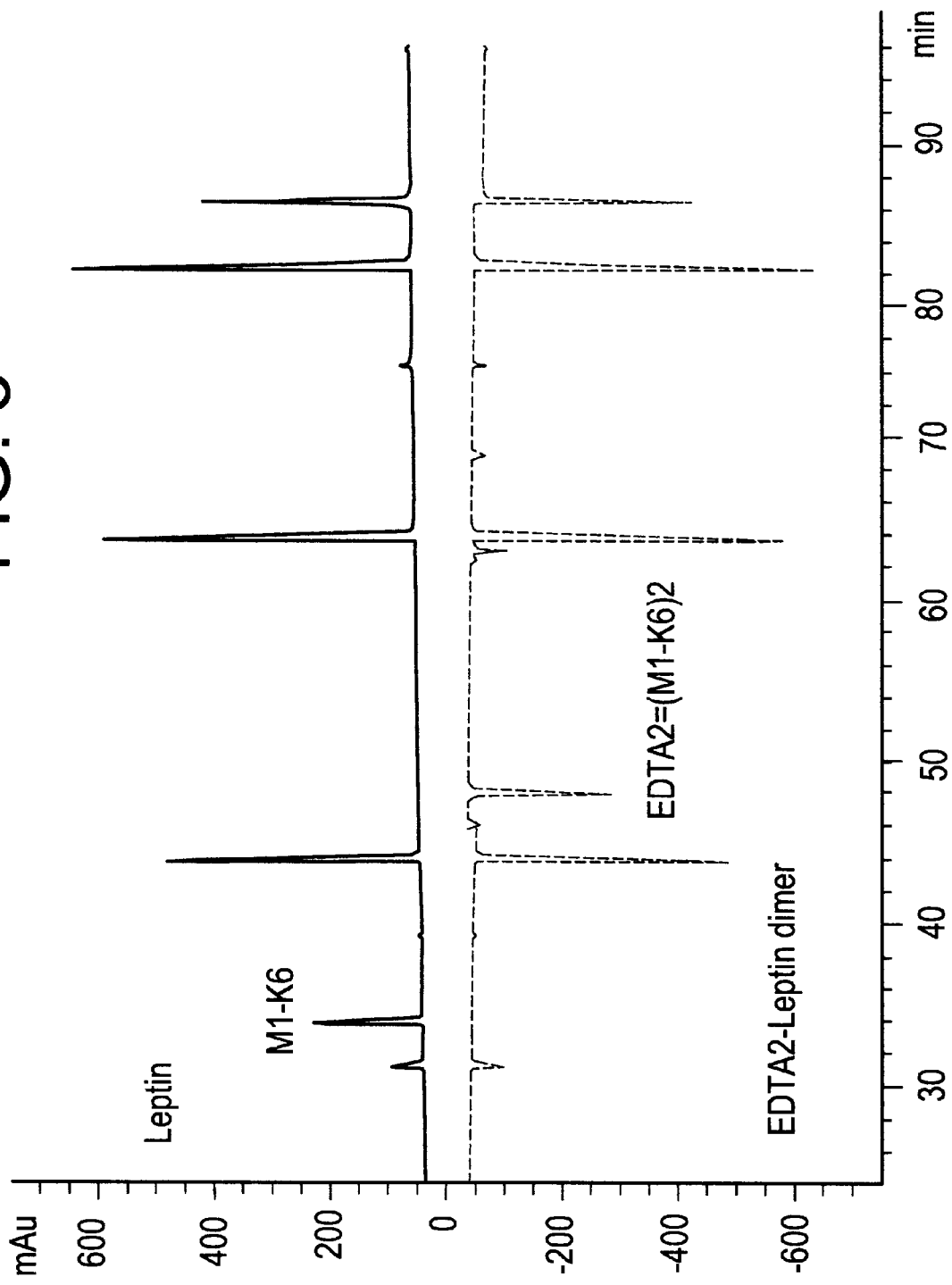
FIG. 8 is a reverse phase HPLC chromatogram of Lys-C digests showing retention time shifts resulting from chemical modifications of the N-terminal peptide (M1–K6) by $EDTA^2$.

Lys-C digests of unmodified leptin and the various modified leptins were performed by reaction of 100 μg of protein with 4 μg of endoproteinase Lys-C (Boehringer Mannheim) in 50 mM Tris-HCl, pH 8.5 (200 μl) for four hours at room temperature. Peptide maps of the various samples were generated by reverse phase HPLC on a 4.6×250 mm, 5μ C4 column (VydaK, Hesperia, Calif.) equilibrated in 0.1% triflouroacetic acid (TFA) with elution over a 0–90% acetonitrile gradient (see FIGS. 6–8). As evidenced by the plots depicted in FIGS. 6–8, only the N-terminal peptide (M1–K6) shows any change in retention time as a result of chemical modification. This result indicates that lysine at position 6 is unmodified and accessible to Lys-C digestion and suggests that the chemical modification occurs at the α-amine of the N-terminus. N-terminal modification is further supported by efforts at N-terminal sequencing which indicate that the N-terminus is blocked (data not shown).

Mass determinations for succinyl-leptin and DTPA- and EDTA$^2$-leptin dimers were made on a Kompact Maldi IV (Kratos, Ramsey, N.J.) using a 12 pmol sample in a sinapinic acid matrix. Each conjugate indicates a single chemical modification per molecule.

TABLE 1

| Conjugate | Expected Mass (Da) | Linker Mass (Da) | Measured Mass (Da) |
|---|---|---|---|
| Unmod. leptin | 16,157 | 0 | 16,156 |
| Succinyl-leptin | 16,258 | 101 | 16,254 |
| DTPA-leptin dimer | 32,671 | 357 | 32,705 |
| EDTA$^2$-leptin dimer | 32,570 | 256 | 32,509 |

Figure 9:
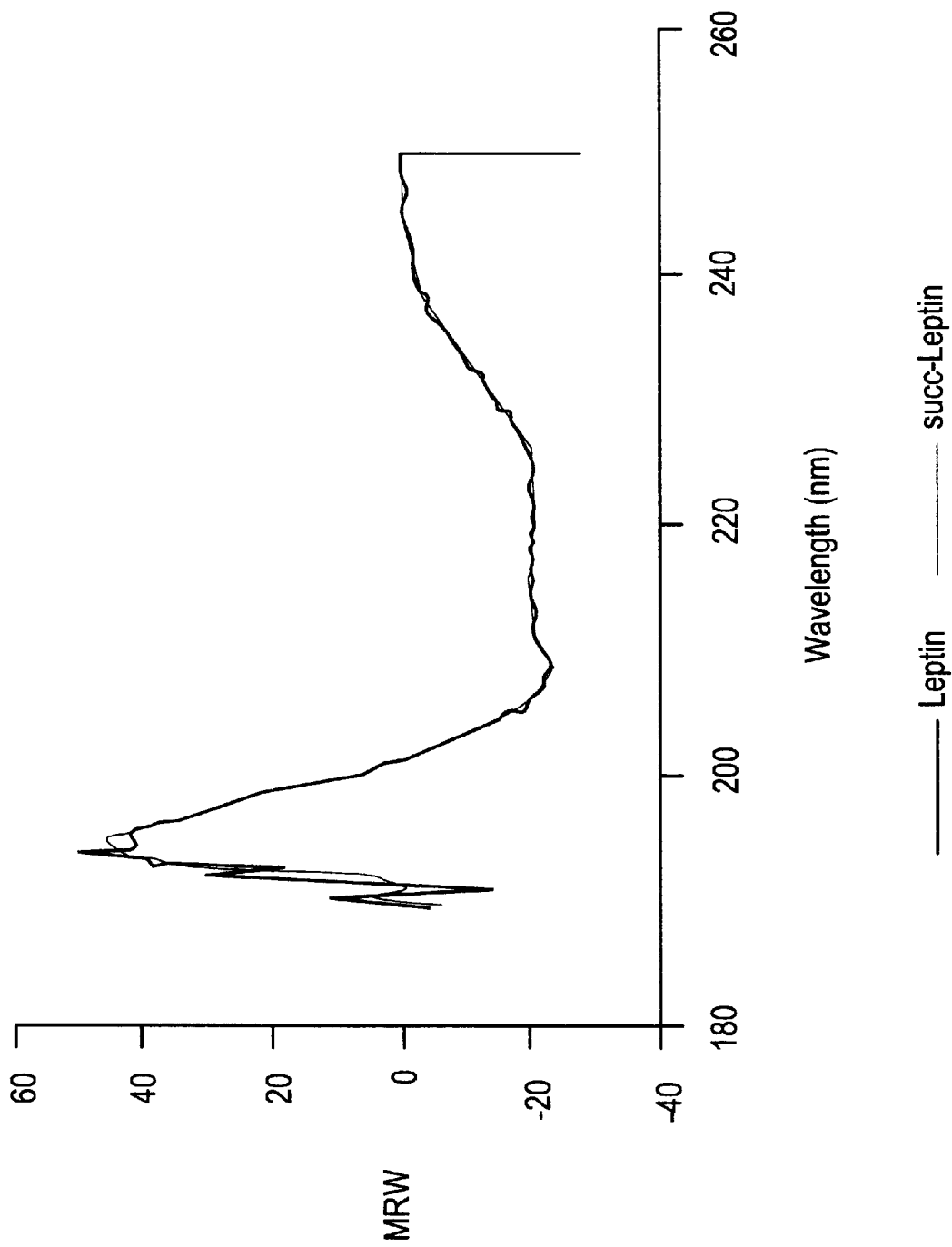
FIG. 9 depicts Far-UV CD spectra of unmodified native leptin and monosuccinylated leptin. Both samples are at 0.25 mg/mL in phosphate buffered saline at ambient temperature.

In addition to the analysis above, the effects on the secondary structure of the succinyl-leptin was evaluated using circular dichroism spectroscopy. Far-UV circular dichroism spectra of unmodified and succinylated leptin in phosphate buffered saline were collected using a 0.05 cm cell in a Jasco J-710 circular dichroism spectrophotometer (Jasco, Tokyo, Japan). The spectra are depicted in FIG. 9 and demonstrate that the secondary structure of succinylated-leptin is preserved.

In sum, the Example 2 data confirms the modification of succinyl-leptin, DTPA-leptin monomers and dimers, and EDTA$^2$-leptin monomers and dimers at the N-terminus, as well as preservation of secondary structure with succinyl-leptin.

EXAMPLE 3

Figure 10:
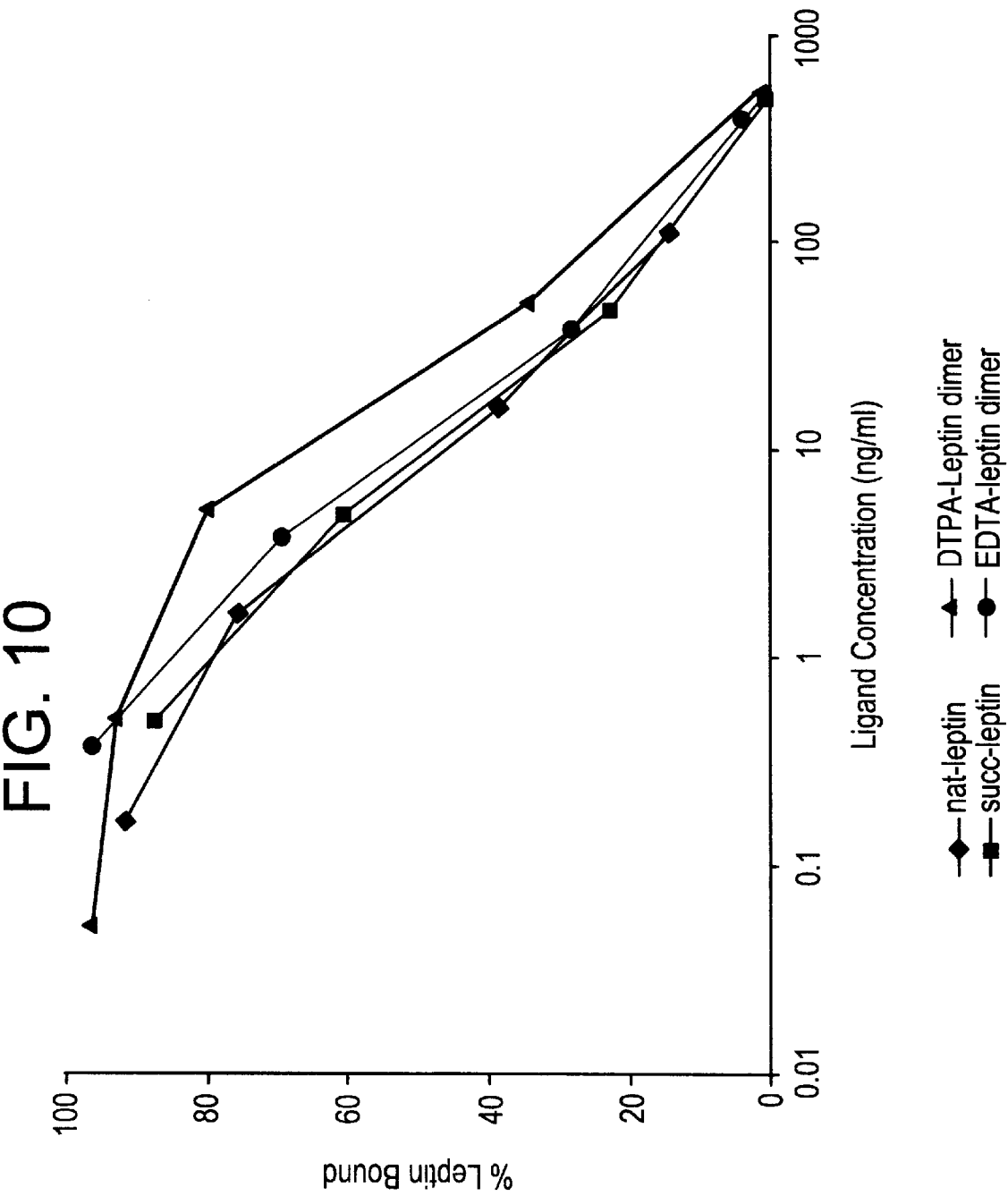
FIG. 10 is a graph depicting in vitro receptor binding of unmodified leptin (-♦-), succinylated-leptin (-■-), DTPA-leptin dimer (-▲-) or $EDTA^2$-leptin dimer (-●-) by displacement of radiolabeled human leptin from immobilized human leptin receptor. Ligand concentration (ng/mL) is plotted versus % ligand bound.

This example describes the receptor binding studies performed on each of the leptin conjugates prepared in Example 1. Each of the leptin conjugates prepared in Example 1 was evaluated using an in vitro receptor binding assay which measures the relative affinity of leptin conjugates based on their ability to displace radiolabeled human leptin from a human leptin receptor expressed in immobilized cell membranes. As evidenced by the FIG. 10 data, the chemically modified isoforms, succinyl-, DTPA-, and EDTA$^2$-leptin each showed relative affinities for human leptin receptor equal to the unmodified leptin over the entire range of ligand binding (~1–100 ng/mL), with $ED_{50}$'s of approximately 10 ng/mL.

The Example 3 data thus show that the monosubstituted succinyl-leptin, monosubstituted DTPA-leptin dimer, and EDTA$^2$-leptin dimer demonstrate preservation of in vitro receptor binding activity as compared to unmodified leptin.

EXAMPLE 4

This example describes the solubility testing performed on each of the leptin conjugates prepared in Example 1. The leptin conjugates were dialyzed into PBS then concentrated with CentriPrep concentrators, 10 kDa molecular weight cutoff (Amicon) to the point that precipitates were observed. The sample was clarified by centrifugation and the conjugate protein concentration in the supernatant determined. The samples were then kept at room temperature ($\approx 22°$ C.) for 48 hours and at regular time points centrifuged and the conjugate protein concentration in the supernatant redetermined. The solubility of the conjugate protein in PBS is thus defined as the steady state protein concentration at room temperature observed in the supernatant after centrifugation (see Table 2).

TABLE 2

| Sample | Maximum Solubility in PBS (mg/ml) |
|---|---|
| unmodified leptin | 3.2 |
| succinyl-leptin | 8.4 |
| DTPA-leptin | 31.6 |
| EDTA$^2$-leptin | 59.9 |

The Table 2 data shows that the monosubstituted succinyl-leptin, monosubstituted DTPA-leptin, and monosubstituted EDTA$^2$-leptin have substantially improved solubility as compared to unmodified leptin, with the monosubstituted EDTA$^2$-leptin showing dramatically enhanced solubility.

EXAMPLE 5

This example describes the in vivo bioactivity studies performed on the leptin conjugates prepared in Example 1. The described leptin conjugates were tested in both mouse and dog animal models to determine bioefficacy relative to the unmodified leptin. Mice were injected daily for 5–7 days with monosubstituted succinyl-leptin, DTPA-leptin dimer, DTPA-leptin monomer and EDTA$^2$-leptin dimer at dosages of 1, 10 and 50 mg/kg body weight. Bioefficacy was measured as a percentage weight loss from day 0, normalized to the vehicle alone control and compared to the weight loss observed with the unmodified protein. All samples for dosages of 1 and 10 mg/kg were formulated in PBS at 0.2 and 2.0 mg/ml respectively. Higher dosages were formulated in PBS at 20–50 mg/ml for the chemically modified forms, however the solubility limits of the unmodified leptin necessitated its formulation at high concentrations in a pH 4 acetate buffer. In addition dogs were injected with 0.05, 0.15 and 0.5 mg/kg daily dosages of succinyl-leptin at 5 mg/ml over 28 days while monitoring weight loss followed by a recovery period.

Figure 11:
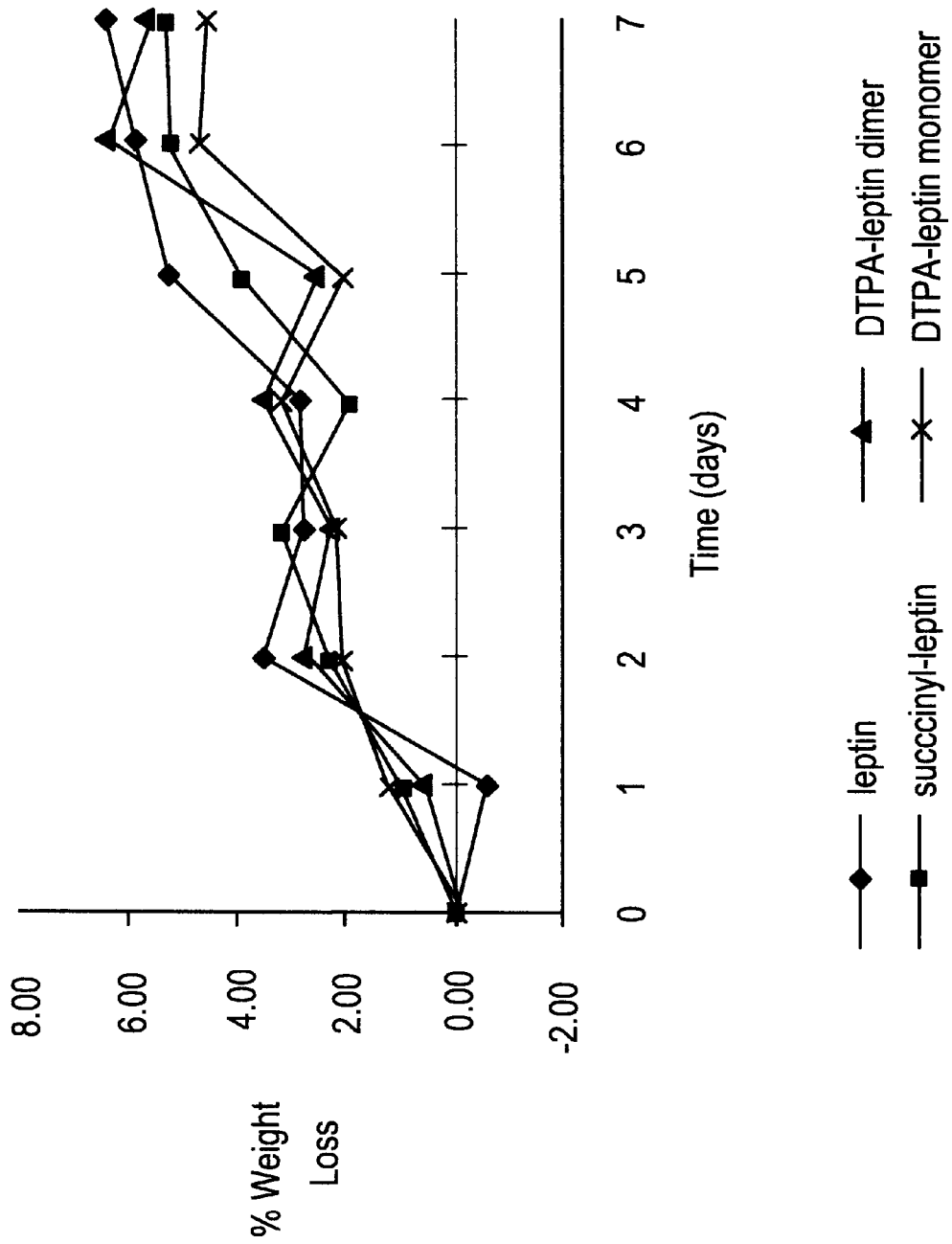
FIG. 11 is a graph depicting weight loss in mice that had been treated with either unmodified leptin (-♦-), succinylated-leptin (-■-), DTPA-leptin dimer (-▲-) or DTPA-leptin monomer (-x-). Mice were dosed daily at 10 mg/kg delivered at 2 mg/mL in PBS. Time (days) is plotted versus % weight loss.

Bioactivity, as judged by drug induced weight loss in animal models, for succinyl leptin was equivalent to the unmodified leptin in both dogs and mice (FIG. 11). Similarly, both DTPA-leptin monomers and dimers and EDTA$^2$-leptin dimers caused equivalent weight loss in mice as compared to the unmodified leptin (FIGS. 11 & 12).

Figure 12:
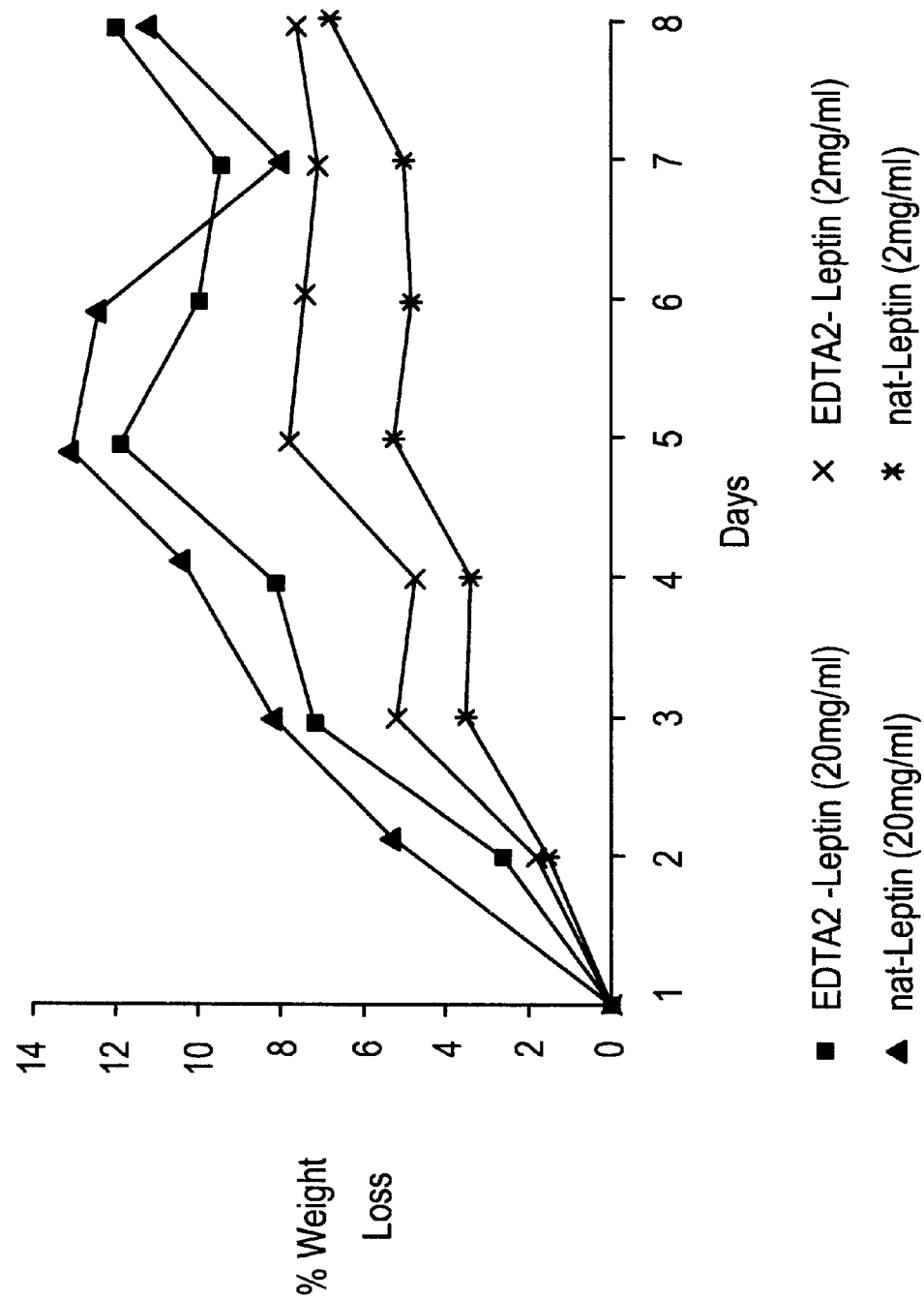
FIG. 12 is a graph depicting weight loss in mice that had been treated with either 20 mg/mL unmodified leptin (-▲-), 2 mg/mL unmodified leptin (-♦-), 20 mg/mL $EDTA^2$-leptin dimer (-■-) or 2 mg/mL $EDTA^2$-leptin dimer (-x-). Mice were dosed daily at 100 mg/kg delivered at 20 mg/mL or 10 mg/kg delivered at 2 mg/mL in PBS (unmodified leptin dosed at 100 mg/kg and 20 mg/mL was formulated in pH 4.0, acetate buffer due to its poor solubility in PBS). Time (days) is plotted versus % weight loss.

The FIG. 11 & 12 data show that the monosubstituted succinyl-leptin, monosubstituted DTPA-leptin monomers and dimers, and EDTA$^2$-leptin dimer demonstrate preservation of in vivo bioefficacy as compared to unmodified leptin.

EXAMPLE 6

This example describes the injection site evaluation performed on the leptin conjugates prepared in Example 1. Tissue sections from the injection sites of three mice from each dosing group were examined histochemically. Injection site pathology's which were identified and scored were necrosis, suppurative (mixed cell infiltrate composed of eosinophils and neutrophils), mononuclear cells (macrophages), leptin precipitates (characterized as either fine ppt. or large deposits/clumps) and giant cells. Each reaction was scored using the following grading system:

| | |
|---|---|
| 0 | Normal |
| 0.5–1 | Minimal change |
| 1.5–2 | Mild change |
| 2.5–3 | Moderate change |
| 3.5–4 | Marked change |
| 4.5–5 | Massive change |

The averaged sum of the scores for each animal were used to define an overall biocompatibility score using the following scoring key:

| | |
|---|---|
| 0–2 | Normal |
| 3–5 | Minimal |
| 6–10 | Mild |
| 11–20 | Moderate |
| 21–30 | Marked |
| >30 | Severe |

Although high concentrations of succinyl-leptin were marginally soluble in PBS at pH 7.0, for the purposes of injection site testing, samples of succinyl-leptin at 20 mg/ml remained soluble in PBS at pH 7.2 and at 50 mg/ml in PBS at pH 7.5. Table 3 shows the injection site evaluation comparing unmodified leptin at 50 mg/mL delivered in pH 4.0, acetate buffer vs. monosubstituted succinyl-leptin at 50 mg/mL in pH 7.5, PBS, after 7 days.

TABLE 3

| Treatment | Dose mg/kg | Volume mL | Necr. | Supp. | Mono. | Fine Precip | Large Deposit | Giant Cells |
|---|---|---|---|---|---|---|---|---|
| Acetate Buf | 0 | 20 | 0 | 0.5 | 1 | 0 | 0 | 1 |
|  | 0 | 20 | 0 | 0 | 0.5 | 0 | 0 | 0 |
|  | 0 | 20 | 0 | 0.5 | 1 | 0 | 0 | 0 |
| Unmod. Leptin | 50 | 20 | 0 | 3 | 2 | 1 | 4 | 1 |
|  | 50 | 20 | 0 | 2.5 | 2 | 1 | 4 | 2.5 |
|  | 50 | 20 | 0 | 1.5 | 2 | 0 | 1.5 | 1 |
| PBS Buffer | 0 | 20 | 0 | 0.5 | 0.5 | 0 | 0 | 0 |
|  | 0 | 20 | 0 | 0.5 | 0.5 | 0 | 0 | 0 |
|  | 0 | 20 | 0 | 0 | 0 | 0 | 0 | 0 |
| Succ-leptin | 50 | 20 | 0 | 1 | 1.5 | 0 | 0 | 0 |
|  | 50 | 20 | 0 | 2 | 1 | 0 | 0.5 | 0.5 |
|  | 50 | 20 | 0 | 1.5 | 0.5 | 0 | 0 | 0 |

As depicted in Table 3, monosubstituted succinyl-leptin, at high concentration dosages, showed improvement in every category of injection site pathology relative to the unmodified leptin, with the most dramatic improvement seen with the almost complete elimination of leptin precipitates and giant cells in the injection sites.

Table 4 shows the injection site evaluation comparing unmodified leptin at 43 mg/mL delivered in pH 4.0, acetate buffer vs. monosubstituted succinyl-leptin at 43 mg/mL in pH 4.0, acetate buffer, after 7 days.

TABLE 4

| Treatment | Dose mg/kg | Volume mL | Necr. | Supp. | Mono. | Precip | Biocomp. Score | Reaction |
|---|---|---|---|---|---|---|---|---|
| Acetate Buf. | 0 | 20 | 0 | 1 | 1 | 0 | 2 | normal |
| | 0 | 20 | 0 | 0 | 0 | 0 | 2 | normal |
| | 0 | 20 | 0 | 0 | 0.5 | 0 | 2 | normal |
| Unmod. leptin | 43 | 20 | 2 | 4 | 3 | 3.5 | 27 | marked |
| | 43 | 20 | 1 | 3 | 3 | 2.5 | 27 | marked |
| | 43 | 20 | 1.5 | 3.5 | 2.5 | 3 | 27 | marked |
| Succ-leptin | 43 | 20 | 0.5 | 2 | 1.5 | 0.5 | 10 | mild |
| | 43 | 20 | 0.5 | 1.5 | 1.5 | 0 | 10 | mild |
| | 43 | 20 | 0 | 1 | 1 | 0 | 10 | mild |

The Table 4 data shows that, surprisingly, it was also observed that high concentrations of monosubstituted succinyl-leptin could be delivered in pH 4, acetate buffer and still demonstrate the dramatic improvements in injection site reactions observed when monosubstituted succinyl-leptin was delivered in PBS.

Table 5 shows the injection site evaluation comparing unmodified leptin at 20 mg/mL delivered in pH 4.0, acetate buffer vs. monosubstituted DTPA-leptin dimer at 20 mg/mL in PBS, after 7 days.

TABLE 5

| Treatment | Dose mg/kg | Volume mL | Necr. | Supp. | Mono. | Precip | Biocomp. Score | Reaction |
|---|---|---|---|---|---|---|---|---|
| Acetate Buf | 0 | 80 | 0 | 0.25 | 1 | 0 | 3 | minimal |
| | 0 | 80 | 0 | 0 | 0.5 | 0 | 1 | normal |
| | 0 | 80 | 0.25 | 0.25 | 1 | 0 | 4 | minimal |
| Unmod. Leptin | 20 | 80 | 0 | 2.5 | 2.5 | 2 | 16 | moderate |
| | 20 | 80 | 0.25 | 3.5 | 3 | 2 | 22 | marked |
| | 20 | 80 | 0.25 | 3 | 3 | 2.5 | 21 | marked |
| PBS Buffer | 0 | 80 | 0 | 0 | 0 | 0 | 0 | normal |
| | 0 | 80 | 0 | 0 | 0.5 | 0 | 1 | normal |
| | 0 | 80 | 0 | 0 | 0 | 0 | 0 | normal |
| DTPA-lep | 20 | 80 | 0.25 | 1.5 | 2 | 0 | 11 | moderate |
| dimer | 20 | 80 | 0 | 1 | 1.5 | 0 | 7 | mild |
| | 20 | 80 | 0 | 1.5 | 2 | 0 | 10 | mild |

Table 6 shows the injection site evaluation comparing unmodified leptin at 20 mg/mL delivered in pH 4.0, acetate buffer vs. monosubstituted $EDTA^2$-leptin dimer at 20 mg/mL in PBS, after 7 days.

TABLE 6

| Treatment | Dose mg/kg | Volume mL | Necr. | Supp. | Mono. | Precip | Biocomp. Score | Reaction |
|---|---|---|---|---|---|---|---|---|
| Acetate Buf | 0 | 100 | 0 | 0.25 | 1 | 0 | 3 | minimal |
|  | 0 | 100 | 0 | 0.5 | 1 | 0 | 4 | minimal |
|  | 0 | 100 | 0 | 0.5 | 1 | 0 | 4 | minimal |
| Unmod. Leptin | 100 | 100 | 0 | 2 | 3 | 3 | 18 | moderate |
|  | 100 | 100 | 0.5 | 2 | 3 | 3 | 18 | moderate |
|  | 100 | 100 | 0 | 2 | 2.5 | 2 | 14 | moderate |
| PBS Buffer | 0 | 100 | 0 | 0 | 0.5 | 0 | 1 | normal |
|  | 0 | 100 | 0 | 0.25 | 0.25 | 0 | 1 | normal |
|  | 0 | 100 | 0 | 0.25 | 0.25 | 0 | 1 | normal |
| EDTA-lep | 100 | 100 | 0 | 1.5 | 2 | 0 | 9 | mild |
| dimer | 100 | 100 | 0 | 1.5 | 1.5 | 0 | 8 | mild |
|  | 100 | 100 | 0.5 | 2.5 | 3 | 0 | 16 | moderate |

As depicted in Tables 5 & 6, DTPA-leptin dimers (Table 5) or EDTA$^2$-leptin dimers (Table 6) can be administered to mice at high concentration in PBS demonstrating the same improvement in injection site pathology as observed with succinyl-leptin. These conjugates however, are substantially more soluble in pH 7, PBS and thus provide for a more rugged formulation in this buffer.

In sum, the Example 6 data shows that the monosubstituted succinyl-leptin, monosubstituted DTPA-leptin monomers and dimers, and EDTA$^2$-leptin monomers and dimers do not precipitate at the injection site when dosed at high concentrations, and importantly, demonstrate substantial improvement in the adverse injection site reactions observed with the unmodified leptin.

Materials and Methods

1. Preparation of recombinant human methionyl-leptin protein

The present recombinant human methionyl-leptin (rhu-met-leptin) may be prepared according to the above incorporated-by-reference PCT publication, WO 96/05309 at pages 151–159. For the present working examples, a rhu-met-leptin was used which has (as compared to the amino acid sequence at page 158) a lysine at position 35 instead of an arginine, and an isoleucine at position 74 instead of an isoleucine. Other recombinant human leptin proteins may be prepared according to methods known generally in the art of expression of proteins using recombinant DNA technology.

While the present invention has been described in terms of certain preferred embodiments, it is understood that variations and modifications will occur to those skilled in the art. Therefore, it is intended that the appended claims cover all such equivalent variations which come within the scope of the invention as claimed.

What is claimed is:

1. Substantially homogenous preparation of monsouccinylated leptin, wherein said monosuccinylated leptin is modified exclusively at the N-terminus.

2. Substantially homogenous preparation of monosuccinylated leptin produced by a process comprising the steps of: (a) reacting leptin with 3–7 fold molar excess of succinic anhydride to form a reaction mixture; (b) stirring said reaction mixture 2–16 hours at 4° C. while maintaining the pH at 7.0; (c) dialyzing said reaction mixture against 20 mM Tris-HCl, pH 7.2; and (d) isolating said monosuccinylated leptin from said reaction mixture, wherein said monosuccinylated leptin is modified exclusively at the N-terminus.

3. A pharmaceutical composition comprising substantially homogenous preparation of monosuccinylated leptin of claim 1 or 2 and a pharmaceutically acceptable carrier.

* * * * *

UNITED STATES PATENT AND TRADEMARK OFFICE
CERTIFICATE OF CORRECTION

PATENT NO. : 5,900,404
DATED : May 4, 1999
INVENTOR(S) : Gegg and Kinstler

It is certified that error appears in the above-identified patent and that said Letters Patent is hereby corrected as shown below:

Column 16,
Line 27, change "monsouccinylated" to -- monosuccinylated --.

Signed and Sealed this

Fifth Day of October, 2004

JON W. DUDAS
*Director of the United States Patent and Trademark Office*